(12) United States Patent
Johnston et al.

(10) Patent No.: US 6,267,967 B1
(45) Date of Patent: Jul. 31, 2001

(54) VIRUS PREPARATIONS AND METHODS

(75) Inventors: Michael Denis Johnston, Cambridge; Roderic Simon O'Keeffe, Essex; Nigel Kenneth Harry Slater, West Midlands, all of (GB)

(73) Assignee: Cantab Pharmaceuticals Research Limited, Cambridge (GB)

( * ) Notice: Subject to any disclaimer, the term of this patent is extended or adjusted under 35 U.S.C. 154(b) by 0 days.

(21) Appl. No.: 09/263,140

(22) Filed: Mar. 5, 1999

(30) Foreign Application Priority Data

Mar. 5, 1998 (GB) .................................................. 9804632

(51) Int. Cl.⁷ ............................ A61K 39/245; C12N 7/02
(52) U.S. Cl. .................................. 424/229.1; 424/231.1; 435/239
(58) Field of Search ...................... 435/239; 424/229.1, 424/231.1

(56) References Cited

U.S. PATENT DOCUMENTS

| | | |
|---|---|---|
| 3,985,615 | 10/1976 | Kubo . |
| 5,024,836 | 6/1991 | McAleer et al. . |
| 5,360,736 | 11/1994 | Provost et al. . |
| 5,447,859 * | 9/1995 | Prussak .............................. 435/239 |
| 5,607,852 | 3/1997 | Provost et al. . |

FOREIGN PATENT DOCUMENTS

| | | |
|---|---|---|
| 209738 | 5/1984 | (DE) . |
| 573107 | 5/1993 | (EP) . |
| 6234659 | 8/1994 | (JP) . |
| WO 92/05263 | 4/1992 | (WO) . |
| WO 94/21807 | 9/1994 | (WO) . |

OTHER PUBLICATIONS

O'Keefe et al (Biotechnology & Bioengineering 57(3):262–271, Feb. 5, 1998).*
Karger et al (J. Virological Methods 70:219–224, Feb. 1998).*
Boursnell et al (J. Infectious Diseases 175:16–25, 1997), Feb. 1998.*
Baba et al., Mechanism of inhibitory effect of dextran sulfate and heparin on replication of human immunodeficiency virus in vitro, Proc. Natl. Acad. Sci. 85:6132–6136 (1988).
E. Lycke et al., Binding of herpes simplex virus to cellular heparan sulphate, an initial step in the adsorption process, Journal of General Virology, 72:1131–1137 (1991).
H. Mitsuya et al., Dextran Sulfate Suppression of Viruses in the HIV Family: Inhibition of Virion Binding to CD4+ cells, Science, 240:646–649 (1988).
O'Neil et al., Virus Harvesting and Affinity–Based Liquid Chromatography, Bio/Technology, 11:173–178 (1993).

* cited by examiner

Primary Examiner—Mary E. Mosher
(74) Attorney, Agent, or Firm—Klarquist Sparkman Campbell Leigh & Whinston, LLP

(57) ABSTRACT

Herpesvirus preparations, e.g. cultured HSV type 2, e.g. genetically disabled virus for vaccine use, can be purified, e.g. for subsequent pharmaceutical formulation, with solid phase affinity reagents containing sulfate- or sulfonate-comprising binding groups, e.g. sulfated polysacharide groups, e.g. heparin or dextran sulfate, and eluting e.g. with salt solutions. The process can be combined with other culture and harvesting steps.

19 Claims, No Drawings

VIRUS PREPARATIONS AND METHODS

FIELD OF THE INVENTION

This invention relates to the production and purification of viruses and to the harvesting and purification of virus preparations from virus-infected cell cultures, for example for experimental and therapeutic purposes, e.g. for the production of pharmaceutical formulations such as virus vaccines. In particular aspects the invention relates to methods and arrangements for the production of preparations of herpesviruses. Other aspects of the invention will be apparent from the description given below.

BACKGROUND OF THE INVENTION AND PRIOR ART

Several methods are known for producing live virus preparations, e.g. herpesvirus preparations, for vaccine and other purposes.

For example, U.S. Pat. No. 3,985,615 (Osaka Res Foundation: T Kubo et al) shows production of live attenuated varicella virus for vaccine use by culture comprising passage in guinea pig primary embryonic tissue cells. U.S. Pat. No. 5,024,836 (Merck: W J McAleer et al) relates to production of lyophilized vaccine preparations based thereon.

DD-209738 (Cent Cerc Bioprep: IV Patrascu) illustrates production of another type of herpesvirus, for use as vaccine against Marek's disease is produced by (a) culturing specific-pathogen-free chicken embryo cells on dextran microspheres; (b) inoculating the culture at 80% confluence with turkey herpes virus strain FC-126 (clone 1, IIIb); (c) collecting the infected cells in SPGA medium (sucrose, phosphate, glutamate, bovine albumin fraction V) when the cytopathic effect is 80%; (d) subjecting the suspension to three ultrasonic pulses of 1 minute duration at 2 minute intervals and centrifuging it to recover a first crop of vaccine; (e) resuspending the sediment in SPCA medium and repeating step (d) to obtain a second crop of vaccine (to increase the vaccine yield by almost 2%); (f) freezing the combined vaccines at −100 deg.C. prior to determining the virus titre; and (g) diluting the SPCA medium and freeze drying.

JP06234659-A (Z H Handai Biseibutsubyo Kenkyukai) describes, in an example, production of herpesviral vaccine on human diploid fibroblast MRC-5 cells cultured in MEM medium at 37 deg.C.: comprising inoculation of varicella virus Oka strain seed virus at a MOI of 0.03 to MRC-5 cells and culture at 37 deg.C. for 2 days. Virus is then suspended in a solution containing 6.4 g NaCl, 0.16 g KCl, 2.3 g Na2HPO4, 12H2O, 0.16 g KH2PO4, 50.0 g sucrose, 1.0 g Na L-glutamate, 2.0 g gelatin, 25.0 g gelatin hydrolysate and 0.1 g EDA-3Na per l.

EP 0 573 107, U.S. Pat. No. 5,360,736 and U.S. Pat. No. 5,607,852 (Merck: P A Friedman et al) describe processes for production of attenuated varicella zoster virus vaccine, including a process for preparing live, attenuated, cell-free varicella-zoster virus (VZV) vaccine that comprises: (a) Culturing VZV infection-susceptible cells, selected from human diploid cells, to confluency in monolayer culture, under conditions of sufficiently high nutrition to achieve a high degree of cell replication, and supplying a non-metabolizable disaccharide; (b) infecting the cells cultured according to step (a) at as close to the point of confluency as possible with as high a multiplicity of infection of VZV-infected cells as practical; (c) maintaining the VZV-infected culture in a state of high nutrition for about 22–96 hours and harvesting at the point of peak infectious VZV production; (d) washing the V/V-infected culture with a physiologic solution, optionally containing a lysosomotropic agent, such as ammonium chloride or chloroquine, prior to harvesting the VZV infected cells; (e) Harvesting the VZV infected cells into a minimal volume of a stablizing solution and either disrupting the cells immediately or freezing the cells for later disruption, (l) Disrupting the VZV-infected cells to optimally release cell-associated VZV, and removing cellular debris, to provide a cell-free VZV preparation. The process discloses use of cell densities of up to ca. 500,000 cells/cm2 in conventional culture vessles. The process is proposed for mass production of live vaccine. Appropriate nutrient medium for growing cells in monolayer culture in that connection is described as consisting essentially of SFRF-2 medium supplemented with between 0.2 mg/mL and 0.4 mg/mL soybean lipid, the cells being selected from MRC-5 cells, WI-38 cells and Vero cells.

WO 92/05263 (Immunology Ltd: S C Inglis et al) and WO 94/21807 (Cantab Pharmaceuticals Research: Inglis et al) are illustrative of the provision of recombinant cells and culture methods for producing genetically disabled herpesvirus such as herpes simplex virus for vaccine purposes.

It is known that herpes simplex virus can bind to cellular surface heparan sulfate (E Lycke et al, J gen Virol (1991) 72: 1131–1137).

Viruses more widely have been shown to bind to sulfonated polysaccharides such as dextran sulfate, heparin and heparan sulfate (M Baba et al, PNAS 1988 85:6132–6136; E Lycke et al, cited above; and H Mitsuya et al Science 1988 240:646–649). It is also known to carry out affinity binding and purification of feline herpesvirus on a sulfonated derivative of beaded, regenerated cellulose with particle diameter of 80 micron and pore structure claimed to reject virus particles (P F O'Neil and E S Balkovic (1993) Bio-Technology 11(2):173–178).

It remains desirable to provide methods for treatment of herpesvirus-containing preparations, especially further purification processes capable of contributing to the manufacture of infectious virus preparations in good yield and purity, e.g. those that are to be used in vaccines.

SUMMARY AND DESCRIPTION OF THE INVENTION

According to an aspect of the invention, preparations of herpesviruses can be usefully purified by affinity purification on a solid phase (affinity binding reagent) that can competitively bind materials with affinity for heparin. The invention is for example especially applicable to infectious preparations of human herpesviruses such as herpes simplex virus (HSV), e.g. HSV type 2, which can tend to remain strongly cell-associated when grown in culture. The affinity reagent carrying the virus, which can be applied from a carrier liquid containing salt (e.g. sodium chloride or other pharmaceutically acceptable salt over about 0.4M) or containing heparin or another sulfated or sulfonated polysaccharide (e.g. in the order of about 10–250, such as about 50, micro-g/ml), can then suitably be washed and the virus recovered in actively infectious form by elution, e.g. with high-concentration salt solution or with sulfated or sulfonated polysaccharide.

Examples of suitable solid phases for use in this connection include a heparin-carrying solid phase, and solid phases with similar binding functionality, e.g. preferbly a sulfated (or sulfonated) polysaccharide binding functionality. Suitable affinity binding reagents can carry binding groups containing sulfate or sulfonate together with nonionic polar groups. For example the sulfated polysaccharides contain sulfate groups and hydroxy groups. Examples of solid phases carrying sulfated polysaccharide include dextran sulfate or heparin sulfate. Preferably, the sulfate or sulfonate groups can be carried on side chains, e.g. polymeric sidechains, relative to the material of the solid phase, and thus can be other than resins and crosslinked polymer beads that have been directly derivatised with such acid groups. Solid phases carrying other sulfate-comprising or sulfonate-comprising binding agents than those already mentioned, such as biphenyl disulfonic acid urea copolymers, or protamine sulfate, can be used.

In a preferred aspect of the invention, the affinity purification can form part of a process for producing purified preparations of herpesviruses, which comprises the steps of (i) culturing host cells infected with the virus, e.g. suitable mammalian host cells such as Vero cells of MRC5 cells, or recombinant cells derived from Vero cells, preferably cultured on microcarriers, and infected with HSV-2 (or in further embodiments, cells infected with other viruses such as VZV), (ii) harvesting the virus from the culture, preferably by an elution process, e.g. using a sulfated polysaccharide eluant such as dextran sulfate or heparin sulfate, or a saline eluant, and (iii) affinity-purifying the harvested virus using a solid phase carrying a sulfated affinity binding agent, preferably one of those identified above, e.g. a sulfated polysaccharide for example heparin, for the virus.

In a further aspect of the invention, a preferred agent for the release of herpesvirus from cell cultures of virus infected cells e.g. Vero cells, comprises dextran sulfate. An example of a dextran sulfate preparation suitable for use in this invention has for example a molecular weight of about 5,000, but a variety of preparations can be chosen.

An example of a suitable form of heparin-carrying solid phase for the affinity purification step comprises Pharmacia Heparin HP column chromatography material (based on a highly cross-linked agarose gel) (e.g. of diameter about 34 micron) obtainable from Pharmacia Biotech in the form of HiTrap (TM) prepared columns. Many other solid phase preparations derived from heparin or heparin sulfate can also be expected to be suitable.

A further and presently preferred example of an affinity binding reagent for use in the invention carries pendent polyacrylemide chains substituted by sulfoisobutyl groups, e.g. comprises groupings such as —$CO.NH.C(CH_3)_2\cdot_2.CH_2.SO_3$—. A suitable and preferred example of such an affinity reagent is for example commercially available from Merck (Darmstadt, Germany) under the designation Fractogel (TM) EMD $SO_3$ 650 (M), and is based on polyacrylemide beads which have been derivatised to provide, covalently attached thereto, pendent polyacrylemide chains in which many of the amide groups are substituted by sulfoisobutyl groups. A further example of a useful affinity binding reagent is a preparation of Sephacryl (I M: Pharmacia) beads having dextran sulfate groups of about $10^6$ m.w. tentacularly attached thereto, i.e. covalently attached thereto and projecting from the surface of the beads.

The invention also provides in another aspect, as an intermediate in the purification of herpesviruses, a preparation of an affinity reagent as set out above, carrying infectious herpesvirus bound thereto.

Thus, preparations or herpesviruses can be usefully purified by affinity purification on a heparin-carrying solid phase, or on a solid phase with similar binding functionality, preferably a sulfated polysaccharide binding functionality, i.e. a solid phase that can competitively bind materials with affinity for heparin. Examples of such solid phases are those carrying polysaccharide, i.e. dextran sulfate or heparan (heparin) sulfate. Alternatively solid phases carrying other sulfate-comprising binding agents such as biphenyl disulfonic acid urea copolymers, or protamine sulfate, can be used.

The affinity purification can for example be carried out using a saline gradient eluant, e.g. from 0.1M to 1.5M buffered NaCl. Alternatively the virus material can be applied in relatively high-salt conditions, e.g. about 0.8M, or in the presence of heparin or dextran sulfate, and the procedure can comprise a wash step at about 0.7M NaCl followed by an elution step at about 1.5M NaCl. There is often no need to dialyse a salt rich virus preparation before applying it to the heparin column. The precise salt concentrations are often not critical in themselves, and can readily be adjusted and optimised according to the details of the other reagents and conditions.

The affinity purification can typically be carried out on a virus preparation that has been obtained from a culture of suitably infected host cells such as Vero cells.

The initial harvesting of virus from such a cell culture can be carried out in any of a variety of ways. Examples of usable (but less preferred) methods include cell rupture, e.g. by freeze-thaw cycles or osmotic stress procedures, e.g. with hypotonic saline or glycerol solutions: somewhat more preferably, a higher virus yield with lesser quantities of contaminating protein can often be obtained using sonication. More preferably, however, the initial harvesting of the viruses from the culture can be carried out without substantial cell breakage, e.g. by using elution by heparin or dextran sulfate or equivalent, or by using elution with saline solution.

It can be convenient to pass such an initially-harvested viral preparation through a membrane filter, e.g. on approximately 5 micron or finer membrane filter, to yield a clarified viral suspension, before the affinity purification.

Using examples of the invention e.g. as described below, it is possible to prepare viral fractions containing usefully reduced levels of DNA and protein relative to the virus titre.

The viral product of the affinity purification can if desired be subjected to any further chosen purification steps. It can be especially useful to include a filter sterilisation step, e.g. with a fine-pore filter of the order of about 0.22 micron pore size.

In presently preferred examples of the present invention, affinity purification can be carried out on the product of a cell culture infected with a herpesvirus, after previous treatment of the culture by a harvesting incubation with a polysaccharide sulfate. e.g. with dextran sulfate or heparin sulfate solution, to yield a virus suspension. The polysaccharide sulfate solution can be contacted with the cell culture, e.g. at a concentration of the order of about 50 micro-gram/ml for heparin sulfate or about 100 micro-gram/ml for dextran sulfate, e.g. in p117 citrate buffer, for a contact period of the order of about three hours, to yield a liquid containing useful virus content and a much reduced content of cells or cell debris by comparison with (for example) the product of ultrasonic disruption. This process can for example be particularly applicable to give an improved yield of virus for the manufacture of live virus vaccine.

Alternatively, but currently less preferred, hypertonic aqueous salt solution can be used at this stage, e.g. sodium chloride, sodium sulfate, potassium chloride, or others. Preferably such a salt solution can comprise sodium chloride at for example about 0.8 to 0.9 M concentration or above. If sodium sulfate is used, concentration can preferably be about 0.4M or above. Other salts can be used, if desired at similar osmolarity or ionic strength to the concentrations indicated above. The virus can often stand up to 1M or 2M salt concentration but in each case, it is preferred not to go too far above the indicated concentration, so as to avoid excessive cellular protein in the saline liquid. Buffering end other constituents can be chosen suitably in accordance with normal practice for handling the viruses concerned.

The harvesting incubation can be carried out with gentle agitation, and preferably is carried out in such a way as to involve no or minimal cell disruption. The cell culture to be treated to the harvesting incubation can be for example a monolayer culture or a microcarrier culture or a roller-bottle culture.

The harvesting polysaccharide sulfate, e.g. dextran sulfate, or salt solution, can be buffered and maintained at a pH and temperature in themselves suitable for the culture of the virus-infected cells, e.g. about pH 7 with citrate buffer and advantageously about 324 deg.C. for herpes virus such as herpes simplex virus.

Contact time between the cultured cells and the harvesting liquid is not specially critical and can for example be in the range of about 2–24 hours. It has been found in connection with certain examples that for example about 4 hours contact time is preferable because it can offer good yield with acceptably low levels of cellular protein.

After contact between the cultured infected cells and the harvesting liquid, the liquid containing the harvested virus particles can be separated by decantation or any other suitable method: the cultured cells themselves can be allowed to remain attached to the surface on which they were cultured, and can be discarded after the separation of the harvesting liquid.

The harvesting liquid can then if desired be treated by filtration and/or centrifugation to remove residual cells.

If desired to change the medium in which the harvested virus preparation is contained, this can be done by dilution or dia-filtration, e.g. to approximately isotonic concentration, e.g. about 138 mM in buffered sodium chloride.

According to a further feature that can be applied to a process according to the invention, the virus preparation harvested in this way can be treated with nuclease enzyme either before (or less preferably after) the affinity purification, to reduce any content of contaminating nucleic acid to acceptable levels.

The virus-containing liquid can for example be treated with Benzonase (TM) nuclease enzyme, to degrade free nucleic acids (importantly DNA, and usually also RNA) at up to about 50 units/ml in the presence of about 2–10 mM magnesium ion, either for up to about 1 hour at from about 4 deg.C. to room temperature.

The level of nuclease enzyme and other protein can then be reduced for example either by the affinity purification step as described herein, or by other means such as for example dia-filtration against a suitable formulation buffer, through a membrane with a 500 kD exclusion limit.

After such treatments the harvested virus can be transferred to a desired carrier liquid, and frozen, freeze-dried/lyophilised or otherwise stabilised in any suitable manner. Generally the herpesvirus can be formulated with a pharmaceutically acceptable carrier or excipient, and optionally sterilised and frozen or freeze-dried, e.g. frozen at about −80 deg.C. for use as a vaccine. Thus the invention can be used in the production of stabilised vaccines containing infectious herpesvirus such as human herpes simplex virus, e.g. HSV type 2, e.g. in the form of a genetically disabled mutant of such virus.

Processes according to examples of the invention can offer particular advantage in connection with highly cell-associated viruses, i.e. those viruses having a particularly high degree of cell association in culture, for example herpes simplex virus type 2 (HSV-2), bovine herpesvirus (BHV), turkey herpesvirus and varicella zoster virus (VZV), sometimes also pseudorabies virus (PRV). With certain herpesviruses and culture conditions (e.g. with herpes simplex virus type 1 (HSV-1) or PRV) there can be a substantial spontaneous release of virus form the infected cells into the cell culture liquid, so that application of a release process stop using sulfated polysaccharide or saline as described herein may be unnecessary, and accordingly examples of the invention can omit such a step before applying the virus-containing liquid form the cell culture to the affinity purification step.

The invention can be applied with any appropriate adaptations of detail as will be readily accessible to those skilled in the art, to herpesviruses of various types, including for example wild-type herpes simplex virus and genetically disabled herpes viruses such as herpes simplex virus, and for example other herpes viruses as mentioned in the documents cited herein.

The virus preparations obtained by the use of processing steps as described herein can be further processed and made part of pharmaceutical compositions e.g. with per-se conventional ingredients of virus vaccines.

The invention is further described and illustrated by the following non-limitative example.

EXAMPLE

A process according to an example of the invention, for harvesting and purifying virus particles, can make use of a culture of Vero cells infected with HSV-2 (e.g. a gH- deletant mutant of HSV2 as described in WO 94/21807 for vaccine use), grown essentially in known manner in conventional culture medium contained in roller bottles at about 100 ml of medium per bottle. The culture medium, cell type and culture conditions can be for example as follows:

The Vero cells can be passaged at $2 \times 10^7$ cells per roller bottle. Culture can be carried out using DMEM medium with 4.5 g/l glucose without sodium pyruvate and with Glutamax-1 (1 M) (L-alanyl-L-glutamine), 862 mg/l. Incubation can be carried out for example at about 37 deg.C. and for about 120 hours (5 days). Confluent cell cultures can then be infected with HSV-2 at a multiplicity of infection of about 0.01, by diluting the virus in DMEM to the level where 1 ml is added to each roller bottle which is then returned to the roller-incubation apparatus at about 34–37 deg.C. When cytopathic effect is observed to be 80–100%, e.g. 65–72 hours after infection, the roller bottles can be treated as ready for virus harvest.

The culture medium can be decanted from each bottle and replaced by 10 ml per bottle of a buffered harvesting solution containing 0.01M sodium citrate pH 7.0 and either about 50 micro-gram/ml of heparin sulfate or about 100 micro-gram/ml of dextran sulfate. The cells in the roller bottle in contact with this buffered harvesting solution can be rolled and incubated at about 34 deg.C. for about 4 hours.

The cultured cells themselves in the roller bottle can largely remain attached to the bottle surface and can be discarded after separation of the liquid containing the harvested virus particles.

The liquid in the bottle, comprising the buffered harvesting solution and material from the cell culture in suspension, including virus, can be removed by pipette and centrifuged at about 3000 rpm in a Sorvall RT6000 (TM) centrifuge for about 10 minutes (e.g. at RCFmax about 1876). The cells in the pellet, and those remaining in the bottle, are discarded (under appropriate virus-containment conditions) and the supernatant is taken by pipette to the next step, which can be continuous flow centrifugation.

Pre-filtration can be carried out e.g. with a filter having a pore size in the range from 0.8–5 micron (not critical) to yield a clarified viral suspension, before the affinity purification. The supernatant liquid from centrifugation can be diluted or diafiltered to a final concentration (in respect of sodium ion) of 138 mM.

(In certain embodiments of the invention, the diluted liquid can if desired optionally be treated with Benzonase (TM) nuclease enzyme, to degrade free nucleic acids (the enzyme currently preferred importantly has DNase activity, and usually also, like Benzonase (TM), it will have RNase activity) at up to about 50 units/ml in the presence of about 2–10 mM magnesium ion, e.g. for up to about 1 hour at a temperature from about 4 deg.C. up to room temperature. However, it can often be found that the affinity purification step can sufficiently reduce the content of DNA in the material that a separate DNase treatment step is unnecessary. Furthermore, if Benzonase or a similar enzyme is employed, some care needs to be used in view of the affinity of the enzyme for heparin and heparin-column and similar materials, it is desirable in such a case to ensure conditions such that the final virus eluate form the affinity column is substantially free from the Benzonase enzyme.)

The intermediate virus-containing liquid can be purified on Pharmacia heparin HP column chromatography material (based on a highly cross-linked agarose gel) (e.g. of diameter about 34 micron) obtainable from Pharmacia Biotech in the form of HiTrap (TM) prepared columns. The rate of virus application can be for example per 5 ml of column material e.g. about 300 ml at a virus concentration of about $8 \times 10^0$ pfu/ml, fed on at a flow rate of about 1.3 ml/min. Using this form of column in one example of this purification step, with a saline gradient starting at about 1.38 mM NaCl and rising to 1.5M NaCl e.g. over about 10 column volumes, viral breakthrough in the eluate occurred at about 230 min of flow, at which point about $3.5 \times 10^0$ pfu had passed into the column and about $1.2 \times 10^8$ pfu had appeared in the eluate. It is expected that up to about $10^{13}$ pfu/ml virus can theoretically be accommodated on this adsorbent column material, in practice say up to about $1-2 \times 10^9$ pfu/ml. alternatively the affinity reagent can be beads of Fractogel (IM) FMD $SO_5$ 650 M from Merck (Darnstadt) as described above, used in generally similar manner, e.g. the virus can be applied in a carrier liquid containing e.g. about 0.8M sodium chloride or 50 microg/ml heparin, and after washing eluted with eluant containing 1.5M sodium chloride.

In a further example of this step, a HSV-2 virus preparation released from Vero cell culture in heparin (Monoporin (TM) injectable pharmaceutical grade heparin of low molecular weight, 50 micro.g/ml in phosphate pH7 10 mM and NaCl 138 mM) was centrifuged at about 3000 rpm (c.1000 g) for 10 minutes, then filtered through a 5 micron filter. A heparin column as already mentioned was prepared by washing with 5 column volumes of phosphate buffered saline. Approximately 100 ml of virus filtrate (about 7×10^7 pfu/ml) was loaded on to the column. After washing with 5–10 column volumes of buffered 0.7M saline, the virus was fractionally eluted with buffered 1.5M saline and the fractions containing the peak indicated by absorption at 280 nm were collected. The resulting product had (per 10^7 pfu virus) less than 2 ng DNA and less than 1 micro g protein, and was collected at a concentration of about 2×10^9 pfu/ml. It could be diluted to isotonic concentration at about 10^8 pfu/ml, and frozen or otherwise stored or used.

It appears that good recovery of virus form the column can be achieved.

In certain (presently less preferred) contexts of use, as an optional further purification step, if desired, the intermediate virus-containing liquid can be subjected to tangential crossflow filtration (diafiltration) e.g. using a filter/membrane with a 500 kD exclusion limit in a Filtron (TM) or other tangential crossflow device, using a recirculation rate of 1000 ml/min, a filtrate rate of 100 ml/min, and a backflush of 100 ml sodium citrate 0.01M pH 7.25 containing 138 mM sodium chloride.

The retantate from the cross-flow ultrafiltration step can optionally if desired be treated by diafiltration against 5–10 volumes of citrate/saline buffer, and the retentate finally subjected to 0.2 micron (sterilising) filtration optionally preceded by filtration with a filter of from about 0.45 micron to 5 micron, using the same buffer again. If desired, this step can be used to make the liquid containing the virus preparation up to about 20 mg/ml in a suitable stabiliser such as a stabilising protein, e.g. human serum albumin at about 20 mg/ml. It can sometimes be useful to prewash the filters with a liquid containing the same stabiliser in the same buffer, before using the filters to treat the virus preparation.

The resulting product can be obtained as a suspension of virus particles in saline buffer and stabiliser such as stabilising protein, in which the level of residual DNA can be satisfactorily low.

The yield from processes such as those described has been found to be usefully good e.g. by comparison with processes involving ultrasonic cell disruption to liberate virus particles, followed by separation of virus particles from cell debris.

The invention can be usefully applied, for example in a preferred embodiment carried out according to the example described above, to the culture and harvesting of genetically disabled HSV-2 virus for vaccine use, which virus has a deletion in respect to the gH gene essential for production of infectious new virus particles, and is culturable on a cell line which is based on Vero cells which have been made recombinant and able to express the viral gH gene which is missing from the viral genome, e.g. as described in specifications WO 92/05263 and WO 94/21807 (and see also A Forrester et al, J Virol 66 (1992) 341–348, also H E Farrell et al. J Virol 68 (1994) 927–932) and C McLean et al. J Infect Dis 170 (1994) 1100–1109).

The present invention and disclosure extend to the methods and compositions and the resulting products as described herein, and to modifications and variations of the steps and features mentioned and described in the present description and claims, including all combinations and subcombinations of the steps and features hereof, including variations in the order and selection of steps, and the documents cited herein are hereby incorporated by reference in their entirety for all purposes.

What is claimed is:

1. A process for purifying a herpesvirus preparation, which comprises (a) culturing host cells infected with the virus, (b) contacting the cells with an eluant without substantial cell breakage, and eluting the virus from said cells in said eluant, (c) contacting the herpesvirus-containing eluate to be purified, with an affinity binding reagent that comprises a solid phase carrying a sulfate or sulfonate-comprising binding group that can bind materials with affinity for heparin, thereby to bind said herpesvirus to the affinity binding reagent, (d) washing said affinity binding reagent carrying said herpesvirus, and (e) eluting said herpesvirus from said binding reagent.

2. A process according to claim 1, comprising the further step of afterwards formulating said herpesvirus with a pharmaceutically acceptable carrier or excipient, and optionally sterilising and freezing or freeze-drying the preparation.

3. A process according to claim 2 wherein the herpesvirus comprises infectious herpesvirus, and the resulting pharmaceutical formation is for use as a vaccine.

4. A process according to claim 2, in which (i) the herpesvirus is applied to the affinity reagent from a liquid containing sodium chloride or other pharmaceutically acceptable salt in a concentration greater than about 0.4 M, or containing sulfated or sulfonated polysaccharides, and (ii) the elution from the affinity reagent is carried out with a saline eluant or a sulfated or sulfonated polysaccharide eluant.

5. A process according to claim 1, wherein said affinity binding reagent carries binding groups containing sulfate and nonionic polar groups.

6. A process according to claim 5, wherein said affinity binding reagent carries heparin or dextran sulfate.

7. A process according to claim 1, wherein said affinity binding reagent carries sulfated polysaccharide groups.

8. A process according to claim 1, wherein said affinity binding reagent carries pendent polyarylamide chains substituted by sulfoisobutyl groups.

9. A process according to claim 1, wherein the herpesvirus preparation is infectious human herpes simplex virus type 2 (HSV-2).

10. A process according to claim 9, wherein the eluant used to eluate virus from the cells comprises sulfated polysaccharide, and wherein the virus is eluted from the affinity binding reagent with a high salt solution.

11. A process according to claim 1, wherein the eluant used to elute virus from the cells comprises a hypertonic salt solution, or comprises sulfated or sulfonated polysaccharide.

12. A process according to claim 1, further comprising separating the cells from their culture medium, after culturing host cells infected with the virus, and prior to contacting the cells with the eluant.

13. A process for purifying a herpesvirus preparation, comprising:

(a) contacting a herpesvirus-containing composition with an affinity binding reagent, thereby to bind the herpesvirus to the affinity binding reagent, wherein the herpesvirus-containing composition is a liquid which comprises sodium chloride or other pharmaceutically acceptable salt in a concentration greater than about 0.4 M, or a liquid which comprises a sulfated or sulfonated polysaccharide, and the affinity binding reagent comprises a solid phase carrying a sulfate- or sulfonate-comprising binding group that can bind materials with affinity for heparin;

(b) washing said affinity binding reagent carrying said herpesvirus; and (c) eluting said herpesvirus from said binding reagent.

14. A process according to claim 13, comprising the further step of afterwards formulating said herpesvirus with a pharmaceutically acceptable carrier or excipient, and optionally sterilizing and freezing or freeze-drying the preparation.

15. A process according to claim 14, wherien the herpesvirus comprises infectious herpesvirus, and the resulting pharmaceutical formulation is for use as a vaccine.

16. A process according to claim 13, wherein said affinity binding reagent carries binding groups containing sulfate and nonionic polar groups.

17. A process according to claim 13, wherein said affinity binding reagent carries sulfated polysaccharide groups.

18. A process according to claim 13, wherein said affinity binding reagent carries pendent polyacrylemide chains substituted by sulfoisobutyl groups.

19. A process according to claim 13, wherein the herpesvirus preparation is infectious human herpes simplex virus type 2 (HSV-2).

* * * * *

UNITED STATES PATENT AND TRADEMARK OFFICE
CERTIFICATE OF CORRECTION

PATENT NO.    : 6,267,967 B1
DATED         : July 31, 2001
INVENTOR(S)   : Johnston et al.

It is certified that error appears in the above-identified patent and that said Letters Patent is hereby corrected as shown below:

Column 1,
Line 39, "2%" should read -- 20% --.

Column 2,
Lines 15-16, "an d04" should read -- and 0.4 --.
Line 63, "preferbly" should read -- preferably --.

Column 5,
Line 7, "end" should read -- and --.
Line 21, "324" should read -- 34 --.

Column 6,
Line 14, "form" should read -- from --.
Line 16, "stop" should read -- step --.
Line 19, "form" should read -- from --.

Column 7,
Line 42, "1.38mM" should read -- 138mM --.
Line 60, "phasphate" should read -- phosphate --.

Column 8,
Line 8, "form" should read -- from --.

Column 9,
Line 31, "polyarylamide" should red -- polyacrylamide --.
Line 38, "eluate" should read -- elute --.

UNITED STATES PATENT AND TRADEMARK OFFICE
CERTIFICATE OF CORRECTION

PATENT NO.    : 6,267,967 B1
DATED         : July 31, 2001
INVENTOR(S)   : Johnston et al.

It is certified that error appears in the above-identified patent and that said Letters Patent is hereby corrected as shown below:

<u>Column 10,</u>
Line 28, "wherien" should read -- wherein --.
Line 37, "polyarylamide" should read -- polyacrylamide --.

Signed and Sealed this

Twenty-second Day of October, 2002

*Attest:*

*Attesting Officer*

JAMES E. ROGAN
*Director of the United States Patent and Trademark Office*